US012790291B2

(12) United States Patent
Kovács et al.

(10) Patent No.: US 12,790,291 B2
(45) Date of Patent: Nov. 10, 2026

(54) INDUSTRIAL PROCESS FOR THE PREPARATION OF HEXANOIC ACID, 6-(NITROOXY)-, (1S,2E)-3-[(1R,2R,3S,5R)-2-[(2Z)-7-(ETHYLAMINO)-7-OXO-2-HEPTEN-1-YL]-3,5-DIHYDROXYCYCLOPENTYL]-1-(2-PHENYLETHYL)-2-PROPEN-1-YL ESTER AND HIGH PURE PRODUCT

(71) Applicant: Nicox SA, Sophia Antipois-Balbonne (FR)

(72) Inventors: Szabolcs Kovács, Budapest (HU); Andrea Sántáné Csutor, Budapest (HU); Irén Hortobágyi, Budapest (HU); Judit Póti, Gyömrő (HU); Gael Ronsin, Strasbourg (FR); Nicoletta Almirante, Milan (IT)

(73) Assignee: NICOX SA, Sophia Antipois-Valbonne (FR)

( * ) Notice: Subject to any disclaimer, the term of this patent is extended or adjusted under 35 U.S.C. 154(b) by 508 days.

(21) Appl. No.: 18/348,185

(22) Filed: Jul. 6, 2023

(65) Prior Publication Data

US 2024/0018096 A1 Jan. 18, 2024

(30) Foreign Application Priority Data

Jul. 7, 2022 (EP) .................................... 22290046

(51) Int. Cl.

| | |
|---|---|
| ***C07C 235/34*** | (2006.01) |
| ***A61K 31/5575*** | (2006.01) |
| ***C07C 231/12*** | (2006.01) |
| ***C07C 231/24*** | (2006.01) |
| ***C07C 405/00*** | (2006.01) |

(52) U.S. Cl.

CPC ........ *C07C 235/34* (2013.01); *A61K 31/5575* (2013.01); *C07C 231/12* (2013.01); *C07C 231/24* (2013.01); *C07C 405/0041* (2013.01); *C07C 2531/02* (2013.01); *C07C 2601/08* (2017.05)

(58) Field of Classification Search

CPC ................ C07C 235/34; C07C 231/12; C07C 405/0041; A61K 31/5575

See application file for complete search history.

(56) References Cited

FOREIGN PATENT DOCUMENTS

| | | | |
|---|---|---|---|
| WO | 2009136281 | A1 | 11/2009 |
| WO | 2019162149 | A1 | 8/2019 |
| WO | 2021023693 | A1 | 2/2021 |
| WO | 2022167070 | A1 | 8/2022 |

*Primary Examiner* — Kamal A Saeed

(74) *Attorney, Agent, or Firm* — ArentFox Schiff LLP

(57) ABSTRACT

The present invention relates to a process for preparing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxy-cyclopentyl]-1-(2-phenylethyl)-2-propen-1-yl ester Compound (I)

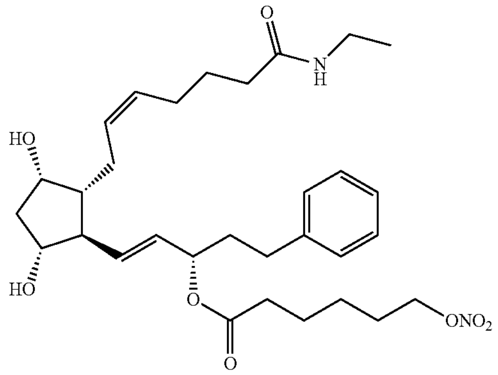

In accordance with the present invention, a pharmaceutical grade Compound (I) can be efficiently prepared by a one-pot reactions preparation step that includes the esterification of the 15-OH bimatoprost by coupling bimatoprost phenylboronate with 6-(nitrooxy)hexanoic acid and the removal of the boronate ester protecting group, followed by an efficient purification step.

The invention refers also to high purity Compound (I) substantially free of the impurity 15-(6-chlorohexanoyl) ester of bimatoprost and to ophthalmic pharmaceutical formulations containing the high purity compound.

6 Claims, No Drawings

INDUSTRIAL PROCESS FOR THE PREPARATION OF HEXANOIC ACID, 6-(NITROOXY)-, (1S,2E)-3-[(1R,2R,3S,5R)-2-[(2Z)-7-(ETHYLAMINO)-7-OXO-2-HEPTEN-1-YL]-3,5-DIHYDROXYCYCLOPENTYL]-1-(2-PHENYLETHYL)-2-PROPEN-1-YL ESTER AND HIGH PURE PRODUCT

CROSS REFERENCE TO RELATED APPLICATIONS

This application claims priority to European Patent Application No. 22290046.6, filed Jul. 7, 2022, the disclosure of which is hereby incorporated by reference in its entirety.

FIELD OF THE INVENTION

The present invention relates to a process, suitable for industrial-scale production. for preparing high purity hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, to high purity hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester substantially free of the impurity 15-(6-chlorohexanoyl) ester of bimatoprost and to ophthalmic pharmaceutical formulations containing the high purity compound.

BACKGROUND OF THE INVENTION

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, also hereinafter referred to as Compound (I), has the following formula (I)

(I)

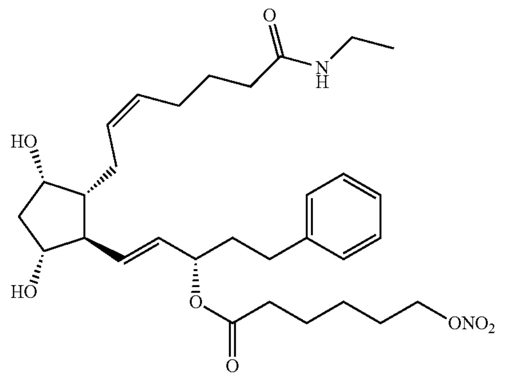

The chemical name of the Compound (I) is also: (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl 6-(nitrooxy)hexanoate.

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is a prostaglandin analogue that has proved effective as IOP-lowering agent (Impagnatiello F, Toris C B, Batugo M, Prasanna G, Borghi V, Bastia E, Ongini E, Krauss A H P; Invest Ophthalmol Vis Sci. 2015; 56:6558-64) and its efficacy as intraocular pressure (IOP) lowering drug in patients with open-angle glaucoma or ocular hypertension has being evaluated.

Studying and monitoring the presence of impurities in Active Pharmaceutical Ingredient(s) (API(s)) is a central topic in drug production in order to ensure proper quality levels in the manufactured products. The limits of each impurity in the produced APIs are the subject of specific guidelines published by international agencies. In the last several years, growing importance has been given to the quantification of potential genotoxic impurities, i.e. those which could cause DNA damage involving genetic mutations. In particular, the limits of impurities bearing one or more alert functions are established according to specific guidelines.

The preparation methods of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester have already been reported; the synthesis methods are disclosed by the original compound patent WO2009/136281 and by the preparation patent applications WO2019/162149 and WO2021/023693. The Compound (I) prepared according to the processes disclosed in WO2019/162149 and WO2021/023693 contains two major impurities that are 15-(6-chlorohexanoyl) ester of bimatoprost of formula (II), which is a potentially genotoxic compound, and 6-{[6-(nitrooxy)hexanoyl]oxy}hexanoic acid bimatoprost ester of formula (III)

(II)

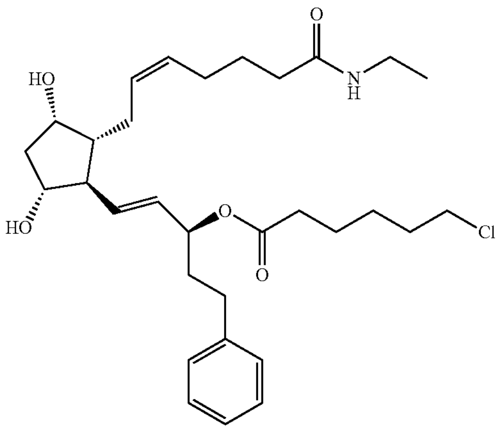

-continued (III)

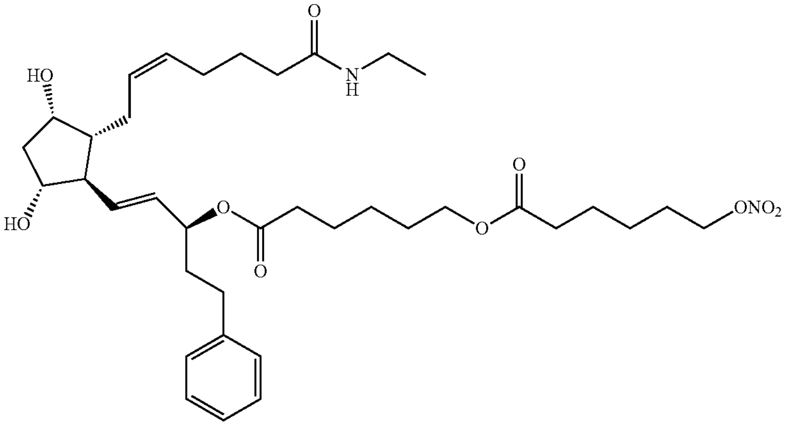

Other known chemical impurities contained in Compound (I) are the isomeric impurities such as (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate that is the 5,6-trans-Compound (I) of formula (VII)

(VII)

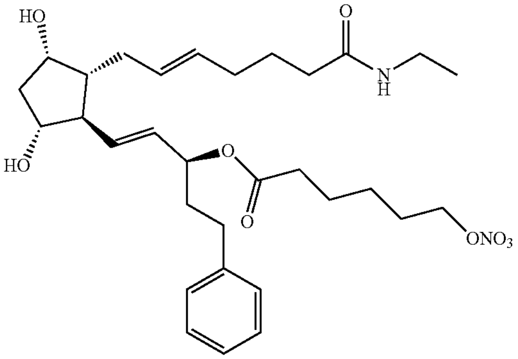

(5,6-trans-Compound (I))

and (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate that is the 15-epi-Compound (I) of formula (VIII)

(VIII)

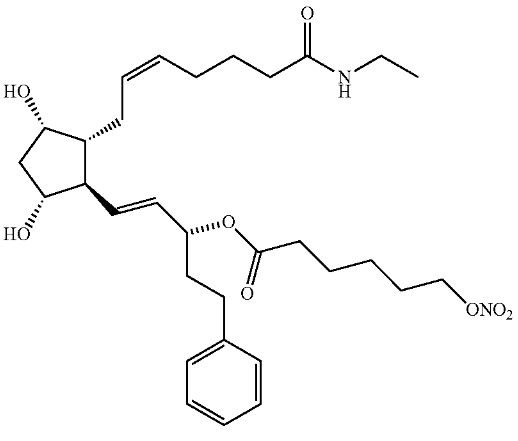

(15-epi-Compound (I))

The presence of these impurities is a critical issue for a large-scale production of pharmaceutical grade Compound (I) because it is an oil and it cannot be purified by crystallization, moreover Compound (I) and the impurities 15-(6-chlorohexanoyl) ester of bimatoprost of formula (II) and 6-{[6-(nitrooxy)hexanoyl]oxy}hexanoic acid bimatoprost ester of formula (III) have similar polarities. Therefore, the removal of these impurities requires several purifications that reduce the yield of the process and increase the cost of the preparation of Compound (I) on a commercial scale.

WO 2019/162149 discloses an industrial process for the preparation of Compound (I). The process includes: the protection of C9-OH and C11-OH of bimatoprost with butyl-boronic acid to form bimatoprost butyl-boronate of formula (IV), (IV)

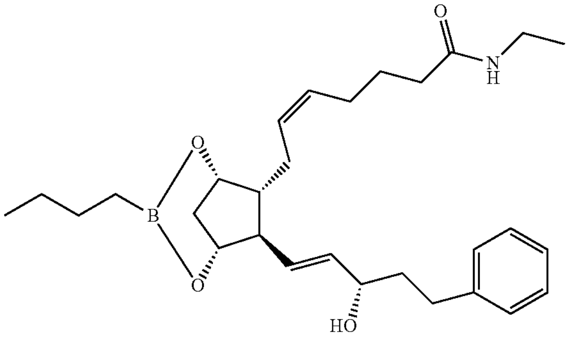

thereafter esterification of C15-OH by reacting bimatoprost butyl-boronate (IV) with 6-(nitrooxy)hexanoyl chloride and removal of the butyl boronate protecting group. The crude Compound (I) is purified by flash chromatography. The 6-(nitrooxy)hexanoyl chloride is synthetized from the 6-(nitrooxy)hexanoic acid that is prepared by a ring-opening reaction of 8-caprolactone and subsequent nitration of the 6-hydroxyhexanoic acid alkali salt with a mixture of $HNO_3$ and $H_2SO_4$ in dichloromethane. The intermediates 6-(nitrooxy) hexanoic acid and 6-(nitrooxy)hexanoyl chloride are used without purification. The obtained Compound (I) contains 0.15% to 0.24% (HPLC area %) of 15-(6-chlorohexanoyl) ester of bimatoprost (II) and 0.40%

(HPLC area %) of 6-{[6-(nitrooxy)hexanoyl]oxy}hexanoic acid bimatoprost ester (III).

The 15-(6-chlorohexanoyl) ester of bimatoprost of formula (II) is a side-product that is formed during the esterification step by exchange reaction of the nitrooxy group of (1E,3S)-1-{(1S,5R,6R,7R)-3-butyl-7-[(2Z)-7-(ethylamino)-7-oxohept-2-en-1-yl]-2,4-dioxa-3-borabicyclo[3.2.1]octan-6-yl}-5-phenylpent-1-en-3-yl 6-(nitrooxy)hexanoate and free chlorine anions; at the end of the process the removal of the boronate ester protecting group leads to 15-(6-chlorohexanoyl) bimatoprost ester.

The 6-{[6-(nitrooxy)hexanoyl]oxy}hexanoic acid bimatoprost ester of formula (III) derives from the reaction of bimatoprost butyl-boronate of formula (IV) with 6-[6-nitrooxyhexanoyl]oxy}hexanoyl chloride that is an impurity of the intermediate 6-(nitrooxy)hexanoyl chloride; after esterification the removal of the butyl-boronate protection leads to 6-{[6-(nitrooxy)hexanoyl]oxy}hexanoic acid bimatoprost ester of formula (III).

WO 2021/023693 disclosed an improvement of the process disclosed in WO 2019/162149 that allows reducing the formation of the 6-{[6-(nitrooxy)hexanoyl]oxy}hexanoic acid bimatoprost ester of formula (III). In this method the 6-(nitrooxy)hexanoic acid is purified by reverse phase chromatography at the end of the nitration step of the 6-hydroxyhexanoic acid alkali salt.

The crude Compound (I) prepared according to the WO 2021/023693 process has a HPLC purity of 73% (HPLC area %) and contains about 0.1% (HPLC area %) of 15-(6-chlorohexanoyl) bimatoprost ester of formula (II) and less than 0.05% (HPLC area %) (HPLC threshold) of 6-{[6-(nitrooxy)hexanoyl]oxy}hexanoic acid bimatoprost ester (III) before the last chromatographic purification.

The synthesis of Compound (I) disclosed in WO 2009/136281 (Example B-1) includes: protection of C9-OH and C11-OH groups of bimatoprost with butyl-boronic acid to form bimatoprost butyl-boronate of formula (IV), esterification of C15-OH with 6-bromohexanoyl chloride to give the 15-(6-bromohexanoyl) ester of bimatoprost butyl-boronate protected form that is converted into the nitrate derivative by silver nitrate in acetonitrile, removal of the butyl-boronate group and purification of the product by reverse phase chromatography. The main drawbacks of the above synthesis are: the use of more than an equimolar amount of 6-bromohexanoyl chloride that has a structural alert for potentially mutagenicity; the use of silver nitrate that generates a large amount of silver salts in waste water, the potential formation of 15-(6-bromohexanoyl) ester of bimatoprost impurity that derives from the incomplete nitration of the intermediate 15-(6-bromohexanoyl) ester of bimatoprost butyl-boronate and the formation of the side-product 15-(6-chlorohexanoyl) ester of bimatoprost of formula (II) that derives from the incomplete nitration of 15-(6-chlorohexanoyl) ester of bimatoprost butyl-boronate. 15-(6-chlorohexanoyl) ester of bimatoprost butyl-boronate is a side-product of the esterification reaction that forms by halogen exchange reaction between the bromine atom of 15-(6-bromohexanoyl) ester of bimatoprost butyl-boronate and free chlorine anions, which form during the esterification step, promoted by the presence of base in the reaction medium.

WO 2009/136281 does not mention the impurities profile of the final product, experiments carried out by the inventors showed that Compound (I) prepared according to the process disclosed by WO 2009/136281 contains about 8.34% (HPLC area %) of 15-(6-chlorohexanoyl) ester of bimatoprost of formula (II).

WO 2009/136281 also discloses an alternative process for the preparation of 15-acylalkynitrate bimatoprost derivatives (Examples N-1 and 0-1). The synthesis comprises reacting bimatoprost in a boronate protected form with a nitrate-alkyl carboxylic acid chloride in the presence of 4-dimethylaminopyridine (DMAP) supported on resin (PS-DMAP), removal of the boronate protecting group and purification by silica gel column chromatography. Although this alternative method avoids the use of 6-bromohexanoyl chloride and the removal of the silver salts, the main disadvantages of the process is the use of 4-dimethylaminopyridine supported on resin that makes the process unsuitable for commercial scale-up and expensive, furthermore, nitrate-alkyl carboxylic acid chloride is added in large excess.

WO2009/136281 also discloses another process (Examples Q1) for the preparation of 15-acylalkynitrate bimatoprost derivatives. In this process the compounds were obtained by esterification of bimatoprost butyl-boronate with an excess of nitrate-alkyl-(p-nitrophenyl)-carboxylate in the presence of 4-dimethylaminopyridine.

The main disadvantage of this synthesis is the removal of the unreacted nitrate-alkyl-(p-nitrophenyl)-carboxylate and of the by-product p-nitrophenol by chromatographic methods.

Thus, there is a need to have high purity hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester which is suitable for the manufacturing of ophthalmic pharmaceutical formulations.

The present invention solve the above the above-mentioned problem providing an industrially viable process for the preparation of high purity hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxy cyclopentyl]-1-(2-phenylethyl)-2-propen-1-yl ester of formula (I).

DESCRIPTION OF THE INVENTION

The present invention provides a process for the synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) (Compound (I)) suitable for industrial scale production and that allows preparing high purity Compound (I) in high yield.

The process of the invention includes an efficient one-pot reactions preparation step of the crude Compound (I) from Bimatoprost and 6-(nitrooxy)hexanoic acid followed by a highly efficient purification step of the crude Compound (I) that includes, first, a normal phase gravity silica gel column chromatography to remove almost all the impurities deriving from the preparation step followed by a silica gel filtration chromatography that has the scope to remove the higher boiling solvents. The process is applicable to a large scale preparation of Compound (I), for example up to 650 grams. An important advantage of the process of the invention is that this process is suitable for the preparation of highly pure hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I), indeed the compound obtained by the process of the invention does not contain the 15-(6-chlorohexanoyl) ester of bimatoprost (II) and the amount of total impurities is not more than (≤) 0.20% (HPLC area %). The high overall chemical yield of the process of about 70% and the high effective purification step make this process a cost-saving method easily applicable to an industrial scale preparation of pharmaceutical grade hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I).

Another object of the invention is hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) substantially free of the impurity 15-(6-chlorohexanoyl) ester of bimatoprost of formula (II) and which contains an amount of total impurities not more than (≤) 0.20% (HPLC area %), preferably the amount of total impurities is not more than (≤) 0.15% (HPLC area %), most preferably the amount of total impurities is not more than (≤) 0.10% (HPLC area %).

The above definitions "does not contain 15-(6-chlorohexanoyl) ester of bimatoprost (II)" and "substantially free of the impurity 15-(6-chlorohexanoyl) ester of bimatoprost of formula (II)" means that the amount of said compound is below the Limit of Detection (LoD) of the HPLC method that is disclosed hereunder.

DETAILED DESCRIPTION OF THE INVENTION

The present invention relates to a process for the preparation of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I)

(I)

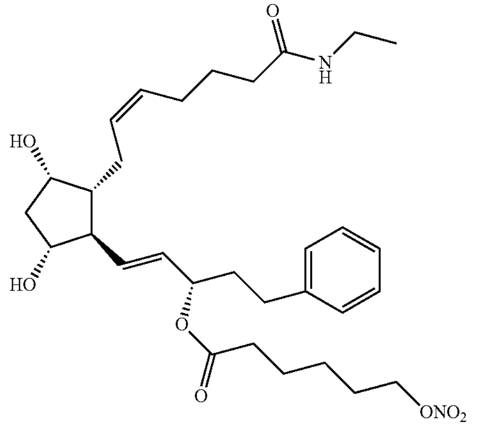

said process comprising the following steps:

1) reacting bimatoprost with phenylboronic acid in toluene at the refluxing temperature and removing water by azeotropic distillation to obtain bimatoprost phenylboronate of formula (V)

(V)

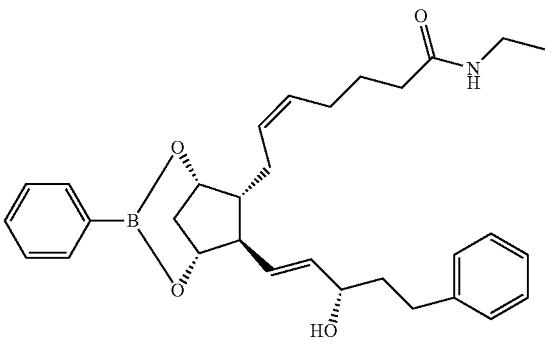

2) cooling down the solution to 25° C. and adding N,N'-diisopropyl carbodiimide, a catalytic amount of dimethylaminopyridine and 6-(nitrooxy)hexanoic acid to obtain (1E,3S)-1-{(1S,5R,6R,7R)-7-[(2Z)-7-(ethylamino)-7-oxohept-2-en-1-yl]-3-phenyl-2,4-dioxa-3-borabicyclo[3.2.1]octan-6-yl}-5-phenylpent-1-en-3-yl 6-(nitrooxy)hexanoate of formula (VI)

(VI)

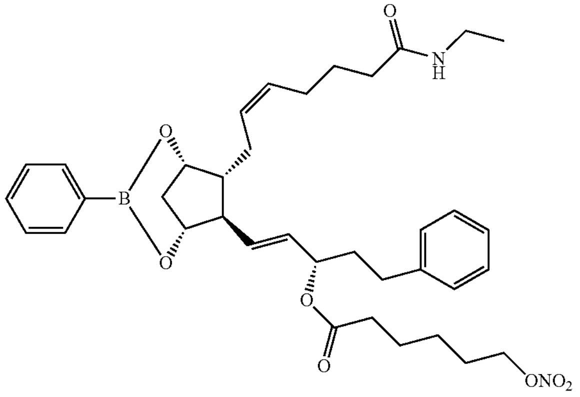

3) removing the phenylboronate protecting group under basic conditions;
4) separating the organic phase, washing the organic phase and evaporating the solvent;
5) stirring the raw product in dichloromethane, filtering the mixture and evaporating the solvent to obtain the crude compound of formula (I);
6) purifying the crude compound of formula (I) by applying a normal phase gravity silica gel column chromatography using an eluent mixture containing diisopropyl ether, acetone and water in 40:15:0.5 volume ratio;
7) collecting the fractions of appropriate purity and evaporating the solvent to obtain pure compound of formula (I);
8) dissolving the pure compound of formula (I) of step 7) in distilled methylene chloride and methanol, purifying the solution by gravity chromatography using an eluent mixture containing distilled methylene chloride and methanol in 30:1 volume ratio; collecting the fractions of appropriate purity and evaporating the solvent;
9) dissolving the pure compound of formula (I) of step 8) in a suitable solvent, treating the obtained solution with activated charcoal and thereafter separating the activated charcoal from the solution by filtration and removing the solvent by evaporation under vacuum to yield pure hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester;

wherein the process is characterized in that the obtained compound of formula (I) does not contain the 15-(6-chlorohexanoyl) ester of bimatoprost of formula (II), and has an amount of total impurities not more than (≤) 0.20% (HPLC area %); preferably the amount of the total impurities is not more than (≤) 0.1% (HPLC area %).

In the reaction step 1), preferably the bimatoprost:phenyl boronic acid molar ratio is 1:1.1, In the reaction step 2) preferably N,N'-diisopropyl carbodiimide 2.0 equiv., dimethylaminopyridine 0.2 equiv. and 6-(nitrooxy)hexanoic acid 1.8 to 2.2 equiv. are added.

In the reaction step 3) the phenylboronate protecting group is preferably removed using a NaOH solution. In particular, the phenylboronate protecting group is removed by quenching the reaction mixture obtained in step 2) with methanol, then adding a mixture of methylene chloride and 6.3 equiv. of NaOH as solution of NaOH 0.5M.

Preferably in reaction step 4) the organic phase is washed first with an aqueous solution of sodium hydrogen sulfate and twice with an aqueous solution of NaCl 15% w/w.

Preferably the process of the invention gives the compound of formula (I) containing not more than (≤) 0.10% (HPLC area %) of total impurities.

Another embodiment of the invention relates to a process for the synthesis of the hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) comprising the following steps:

1) reacting bimatoprost (1 equiv.) with phenyl boronic acid (1.1 equiv.) in toluene to protect the 9,11-hydroxy groups of bimatoprost; warming the reaction mixture to the reflux temperature of toluene to remove by water azeotropic distillation and stirring the reaction mixture at reflux temperature until formation of bimatoprost phenyl-boronate of formula (V);
2) cooling down the reaction mixture to 25° C. and adding N,N'-diisopropyl carbodiimide (2.0 equiv.), a catalytic amount of dimethylaminopyridine (0.2 equiv.) and 6-(nitrooxy)hexanoic acid (1.8 to 2.2 equiv.) to obtain (1E,3S)-1-{(1S,5R,6R,7R)-7-[(2Z)-7-(ethylamino)-7-oxohept-2-en-1-yl]-3-phenyl-2,4-dioxa-3-borabicyclo[3.2.1]octan-6-yl}-5-phenylpent-1-en-3-yl 6-(nitrooxy)hexanoate of formula (VI);
3) at the end of the esterification, quenching the reaction mixture with methanol, then adding methylene chloride and a solution of NaOH 0.5 M, thereafter, stirring the resulting mixture to complete the removal of the phenylboronate protecting group, wherein preferably 6.3 equiv. of NaOH are used;
4) separating the organic phase and washing the organic phase first with an aqueous solution of sodium hydrogen sulfate and twice with an aqueous solution of NaCl 15% w/w thereafter evaporating the solvent at a temperature below 45° C.
5) adding dichloromethane to the raw mixture and stirring the mixture at 10° C. for 30 minutes, removing N,N'-diisopropyl urea by filtration and evaporating the solvent of the filtered solution to obtain the crude compound of formula (I);
6) purifying the crude compound of formula (I) by applying normal phase gravity silica gel column chromatography using an eluent mixture containing diisopropylether/acetone/water in 40:15:0.5 volume ratio;
7) collecting the fractions of appropriate purity and evaporating the solvent to obtain pure compound of formula (I);
8) dissolving the pure compound of formula (I) obtained in step 7) and purifying the solution by gravity chromatography on a column packed with silica using an eluent mixture containing distilled methylene chloride/distilled methanol in 30:1 volume ratio; collecting the fractions of appropriate purity and evaporating the solvent to obtain pure compound of formula (I) as an oil;
9) dissolving the pure compound of formula (I) obtained in step 8) in ethanol, treating the obtained solution with activated charcoal, thereafter removing the activated charcoal by filtration and removing ethanol by evaporation under vacuum leading to the final pure compound of formula (I), wherein the process is characterized in that the obtained compound of formula (I) does not contain the 15-(6-chlorohexanoyl) ester of bimatoprost of formula (II), and has an amount of total impurities not more than (≤) 0.20% (HPLC area %); preferably the amount of the total impurities is not more than (≤) 0.10% (HPLC area %).

The above “equiv.” (equivalent) means the molar equivalent of each reagent and it is calculated with respect to the moles of bimatoprost.

The above reported process is illustrated in the following Scheme.

Scheme of the process

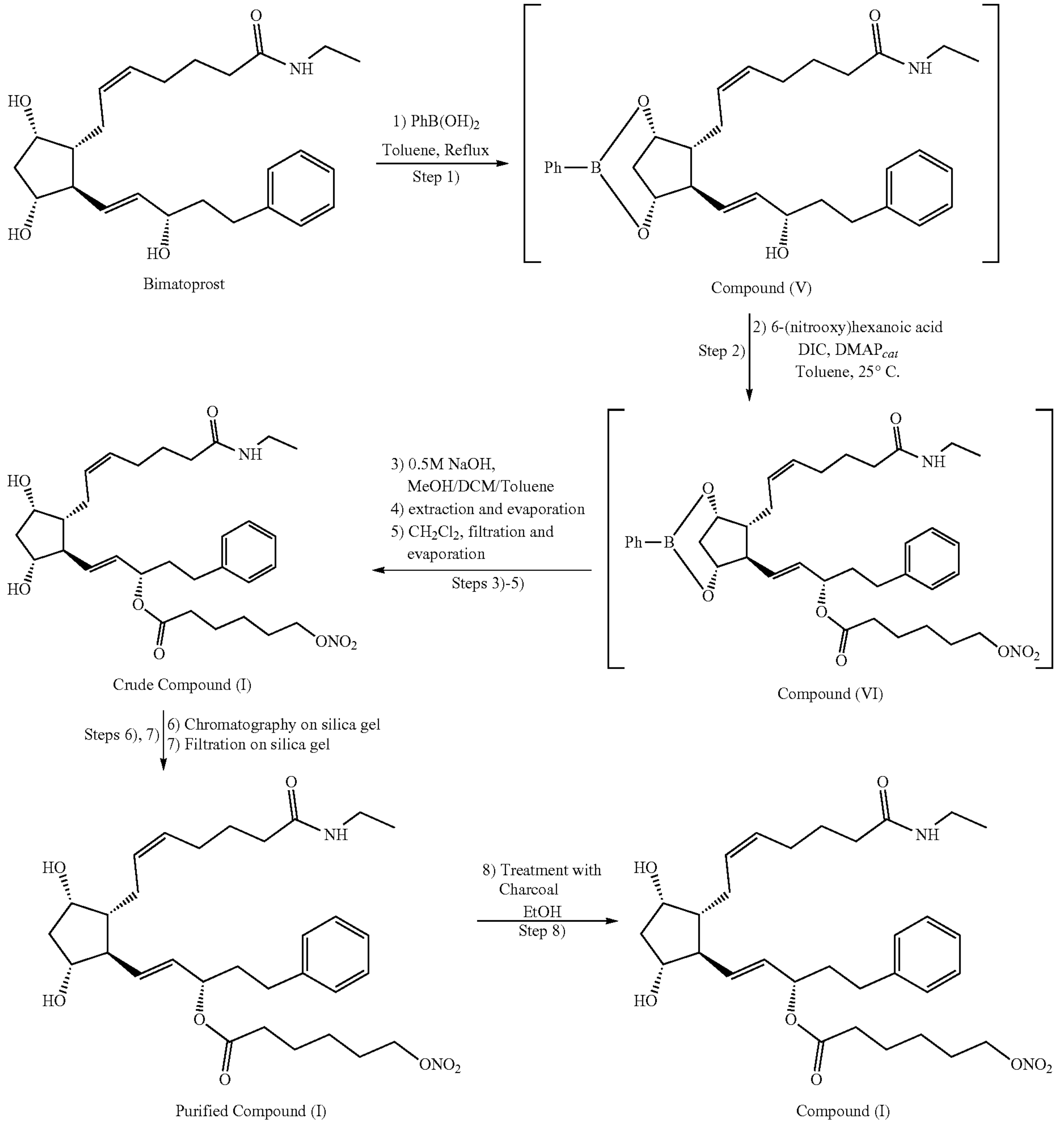

The process of the invention has several advantages, it allows eliminating the formation of 15-(6-chlorohexanoyl) ester of bimatoprost of formula (II) and reducing the amount of 6-{[6-(nitrooxy)hexanoyl]oxy}hexanoic acid bimatoprost ester of formula (III) to below the limit of quantification that is 0.05% w/w. Moreover, the purity assessment of Compound (I) performed by HPLC showed that also the amount of each of impurities 5,6-trans-Compound (I) of formula (VII) and 15-epi-Compound (I) of formula (VIII) is not more than (≤) 0.05% w/w.

Another advantage of the invention process is that the synthesis of the crude compound of formula (I) can be performed in a one-pot reactions preparation in which the above reported steps 1) to 3) are conducted without isolating or purifying the resulting intermediates.

The present invention provides hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) does not contain of the impurity 15-(6-chlorohexanoyl) ester of bimatoprost of formula (II) and which contains an amount of total impurities not more than (≤) 0.20% (HPLC area %), preferably the amount of total impurities is not more than (≤) 0.15% (HPLC area %), most preferably the amount of total impurities is not more than (≤) 0.10% (HPLC area %).

An embodiment of the invention provides hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) that does not contain 15-(6-chlorohexanoyl) ester of bimatoprost of formula (II), wherein said compound of formula (I) contains:

not more than (≤) 0.05% w/w 6-{[6-(nitrooxy)hexanoyl]oxy}hexanoic acid bimatoprost ester of formula (III);

not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)); and not more than (≤) 0.05% w/w (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)); and wherein the amount of total impurities is not more than (≤) 0.20% (HPLC area %).

Another embodiment of the invention provides hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxy cyclopentyl]-1-(2-phenylethyl)-2-propen-1-yl ester of formula (I) that does not contain 15-(6-chlorohexanoyl) ester of bimatoprost of formula (II), wherein said compound of formula (I) contains:

less than (<) 0.05% w/w 6-{[6-(nitrooxy)hexanoyl]oxy}hexanoic acid bimatoprost ester) of formula (III);

not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)); and less than (<) 0.05% w/w (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)); and wherein the amount of total impurities is not more than (≤) 0.20% (HPLC area %).

Another embodiment of the invention provides hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxy cyclopentyl]-1-(2-phenylethyl)-2-propen-1-yl ester of formula (I) that does not contain 15-(6-chlorohexanoyl) ester of bimatoprost of formula (II), wherein said compound of formula (I) contains:

less than (<) 0.05% w/w 6-{[6-(nitrooxy)hexanoyl]oxy}hexanoic acid bimatoprost ester) of formula (III);

not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)); and less than (<) 0.05% w/w (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)); and wherein the amount of total impurities is not more than (≤) 0.15% (HPLC area %).

Another embodiment of the invention provides hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxy cyclopentyl]-1-(2-phenylethyl)-2-propen-1-yl ester of formula (I) that does not contain 15-(6-chlorohexanoyl) ester of bimatoprost of formula (II), wherein said compound of formula (I) contains:

less than (<) 0.05% w/w 6-{[6-(nitrooxy)hexanoyl]oxy}hexanoic acid bimatoprost ester) of formula (III);

not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)); and less than (<) 0.05% w/w (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)); and wherein the amount of total impurities is not more than (≤) 0.10% (HPLC area %).

Another embodiment of the invention provides an ophthalmic pharmaceutical composition comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) that does not contain (15-(6-chlorohexanoyl) ester of bimatoprost of formula (II), and which contains an amount of total impurities not more than (≤) 0.20% (HPLC area %) and at least a pharmaceutically acceptable excipient, preferably the amount of total impurities is not more than (≤) 0.15% (HPLC area %), most preferably the amount of total impurities is not more than (≤) 0.10% (HPLC area %).

Another embodiment of the invention provides ophthalmic pharmaceutical compositions comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) that does not contain (15-(6-chlorohexanoyl) ester of bimatoprost of formula (II), wherein said compound of formula (I) contains: not more than (≤) 0.05% w/w 6-{[6-(nitrooxy)hexanoyl]oxy}hexanoic acid bimatoprost ester of formula (III), not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)), not more than (≤) 0.05% w/w and (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)), wherein the amount of total impurities is not more than (≤) 0.20% (HPLC area %), and at least a pharmaceutical acceptable excipient.

Another embodiment of the invention provides an ophthalmic pharmaceutical composition comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) that does not contain (15-(6-chlorohexanoyl) ester of bimatoprost of formula (II), wherein said compound of formula (I) contains: less than (<) 0.05% w/w 6-{[6-(nitrooxy)hexanoyl]oxy}hexanoic acid bimatoprost ester of formula (III), not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)), less than (<) 0.05% w/w (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)), and wherein the amount of total impurities is not more than (≤) 0.20% (HPLC area %) and at least a pharmaceutical acceptable excipient.

Another embodiment of the invention provides ophthalmic pharmaceutical compositions comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) that does not contain 15-(6-chlorohexanoyl) ester of bimatoprost of formula (II), wherein said compound of formula (I) contains: less than (<) 0.05% w/w 6-{[6-(nitrooxy)hexanoyl]oxy}hexanoic acid bimatoprost ester of formula (III), not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)), less than (<) 0.05% w/w (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)), and wherein the amount of total impurities is not more than (≤) 0.15% (HPLC area %) and at least a pharmaceutical acceptable excipient.

Another embodiment of the invention provides ophthalmic pharmaceutical compositions comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) that does not contain 15-(6-chlorohexanoyl) ester of bimatoprost of formula (II), wherein said compound of formula (I) contains: less than (<) 0.05% w/w 6-{[6-(nitrooxy)hexanoyl]oxy}hexanoic acid bimatoprost ester of formula (III), not more than (≤) 0.05% w/w (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate of formula (VII) (5,6-trans-Compound (I)), less than (<) 0.05% w/w (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate of formula (VIII) (15-epi-Compound (I)), and wherein the amount of total impurities is not more than (≤) 0.10% (HPLC area %) and at least a pharmaceutical acceptable excipient.

The purity and the impurity profile of Compound (I) were assessed by HPLC methods disclosed hereunder (Method 1 and Method 2).

The above reported definitions "does not contain 15-(6-chlorohexanoyl) ester of bimatoprost" or "substantially free of 15-(6-chlorohexanoyl) ester of bimatoprost" mean that the amount of 15-(6-chlorohexanoyl) ester of bimatoprost is below the Limit of Detection (LoD) of the HPLC method disclosed hereunder.

The above reported definition "the amount of 6-{[6-(nitrooxy)hexanoyl]oxy}hexanoic acid bimatoprost ester is less than 0.05% w/w" means that the amount of 6-{[6-(nitrooxy)hexanoyl]oxy}hexanoic acid bimatoprost ester is below the Limit of Quantification (LoQ) of the HPLC method disclosed hereunder.

The above reported definition "the amounts of 5,6-trans-Compound (I) is less than 0.05% w/w" means that the amount of 5,6-trans-Compound (I) is below the Limit of Quantification of the HPLC method disclosed hereunder.

The above reported definition "the amounts of 15-epi-Compound (I) a less than 0.05% w/w" means that the amount of 15-epi-Compound (I) is blow the Limit of Quantification of the HPLC method disclosed hereunder.

Example 1

Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (Compound (I))

The starting material bimatoprost is commercially available.

1a) Preparation of 6-(nitrooxy)hexanoic acid

Synthesis of methyl 6-hydroxyhexanoate

Dry methanol (300 mL) was charged in a 1 L three-necked flask equipped with thermometer, dropping funnel, reflux condenser and magnetic stirrer followed by conc. sulfuric acid (2.8 mL, 0.052 mole 0.06 eq). The mixture was heated to reflux temperature (T=63° C.). To the mixture was added dropwise a solution of F-caprolactone (100 g, 0.876 mole, 1 eq) in dry methanol (200 mL). The reaction was stirred for 2 hours at reflux temperature. TLC was performed to monitor residual F-caprolactone. Reaction mixture was then cooled down to 0-5° C. Conc. $NaHCO_3$ solution (100 mL) was slowly added keeping the temperature below 10° C. The volatile solvent was removed on rotary evaporator under vacuum at temperature of 40° C. To the residue were added water and methyl tert-butyl ether (MTBE) (300 mL). The phases were stirred for 5 minutes, then separated. The aqueous phase was extracted with MTBE (2×200 mL). The combined organic phase was washed with brine (2×100 mL). The organic phase was dried over $Na_2SO_4$, then concentrated on rotary evaporator under vacuum at temperature of 40° C. to obtain methyl 6-hydroxyhexanoate as a colorless oil (103.58 g, Y: 80.9%). GC purity: 96.2%.

Synthesis of methyl 6-nitrooxyhexanoate

Conc. sulfuric acid (45.6 mL 0.85 mol, 3.1 eq) which was cooled to 0-5° C. was added to a 500 mL three-necked flask equipped with thermometer, dropping funnel and magnetic stirrer. Then fuming nitric acid (47.2 mL, 1.12 mol, 4.1 eq) was added dropwise to it while the temperature was kept between 0-5° C. To the cooled mixture was added slowly dry dichloromethane (100 mL, 2.5 V) then stirred between 0-5° C. for 30 min. At this temperature methyl 6-hydroxyhexanoate (40 g, 0.27 mol, 1 eq.) in dry (dichloromethane) DCM (100 mL) was added for 1 hour. After 30 min stirring at 0-5° C. the reaction mixture was monitored by TLC which showed the completed reaction. The reaction mixture was quenched by dropping it to cooled water (200 mL) (T<10° C., −2 hours). Then the phases were separated. The organic phase was dried over $Na_2SO_4$, then concentrated on rotary evaporator under vacuum at temperature of 40° C. to obtain methyl 6-nitrooxyhexanoate (49.46 g). as a yellow oil in a 94.5% yield.

Synthesis of crude 6-(nitrooxy)hexanoic acid 1.5 M NaOH aqueous solution (208 mL) was charged into a 1 L three-necked flask equipped with thermometer, dropping funnel and magnetic stirrer. Methyl 6-nitrooxyhexanoate (49.64 g, 0.26 mol, 1 eq) dissolved in methanol (248 mL, 5V) was added dropwise at room temperature (Tmax=35° C.). After the addition, the mixture was stirred for 2 hours at room temperature. Controlled by TLC the reaction mixture showed the reaction was completed. The pH of the reaction mixture was set to 2.5 using 183 mL 2M HCl aqueous solution. The resulted mixture was extracted with MTBE (100 mL) then the water phase was extracted MTBE (5×50 mL). The combined organic phase was washed with brine (2×30 mL), then concentrated on rotary evaporator under vacuum at temperature of 40° C. to obtain crude 6-(nitrooxy) hexanoic acid as a yellow oil (44.2 g). Assay is assessed by UPLC method.

Purification of 6-(nitrooxy)hexanoic Acid

The crude 6-(nitrooxy)hexanoic acid was purified by column chromatography according to the following procedures:

Eluent was prepared by mixing toluene and methanol in a volumetric ratio of 40:1. Silica was stirred with eluent in a slurry dispenser and the column was loaded and prepared. The crude material (1161 g, assay of 91.8% by UPLC) was dissolved in toluene and the solution was loaded on the top of the column. The elution was performed at a flow rate of 15±5 L/h and fractions of 10 L were collected and analyzed by TLC. Purest fractions were combined and concentrated under vacuum at temperature below 55° C.±5° C. The purified 6-(nitrooxy)hexanoic acid (952 g, 5.37 mole) was isolated as an oil in a 82% yield having a 98.7% purity by UPLC and containing a not detectable amount of 6-[6-nitrooxyhexanoyl]oxy}hexanoic acid.

1b) Synthesis of crude hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (Compound (I))

Toluene (28 Kg, 49 vol) was charged in a reactor followed by Bimatoprost (663 g, 1.595 mol, 1 equiv) and phenylboronic acid (214 g, 1.755 mole, 1.1 equiv). The reaction is heated at 110° C.±5° C. and vapor temperature was maintained at 90° C. for 4 hours to ensure azeotropic distillation of water for a total volume of solvent of around 12 L. Reaction mixture was then cooled down to 25° C.±5° C.

Dimethylaminopyridine (DMAP) (39 g, 0.319 mole, 0.2 equiv) and N,N'-diisopropyl carbodiimide (DIC) (403 g, 3,190 mole, 2.0 equiv) were added to the cooled reaction mixture, followed by a solution of 6-(nitrooxy)hexanoic acid (565 g, 3.190 mole, 2.0 equiv) in toluene (0.5 L, 0.75 vol). The reaction was stirred for 1 to 3 hours at 25° C.±5° C. TLC was performed to monitor residual bimatoprost phenylboronate (Compound (V))

The reaction mixture was quenched with methanol (1.3 L, 2 vol) and was stirred 5 to 10 min The reaction mixture was then transferred via vacuum into an extractor containing 0.5M sodium hydroxide solution (20 L) and dichloromethane (10 L, 15 vol). Reactor was washed with several portions of methylene chloride that were added to the reaction mixture. The reaction mixture was stirred for 2 to 3 hours, then left to settle for 60 min and the organic phase was collected in a mobile tank. Dichloromethane (10 L, 15 vol) was charged into the extractor, the mixture was stirred for 5 to 10 min and left to settle for 15 min. The organic layer was collected. The organic layers were charged again in the extractor and a 1M $NaHSO_4$ solution (20 L) was transferred via vacuum into the extractor. The mixture is stirred for 5 to 10 min, left to settle for 15 min and the lower organic phase was collected in a mobile tank. The aqueous layer was removed. The organic phase was charged again in the extractor and a 15% NaCl solution (20 L) was added and the mixture was stirred for 5 to 10 min and left to settle for 15 min. The organic layer was collected and the aqueous phase was removed. The organic layer was charged again in the extractor and a 15% NaCl w/w solution (20 L) was added. The mixture was stirred for 5 to 10 min and left to settle for 15 min. The organic layer was collected evaporated under vacuum at a temperature of 45° C.±5°

The crude product was dissolved in dichloromethane (7 L, 10.5 vol) and the mixture was transferred into a reactor. The mixture was cooled to 5-10° C. and kept for 30-60 min at this temperature to allow N,N'-diisopropyl urea precipitation. The mixture is filtered through the filter in a mobile tank. The reactor is washed with dichloromethane (2 L, 3 vol), solution is filtered and collected in the mobile tank. Then the solution in the mobile tank is transferred to a flask and the solvent is evaporated under vacuum at temperature of 45° C.±5° C. to obtain the crude hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (crude Compound I).

1c) Purification of the crude hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (Compound (I))

First Chromatography

The eluent mixture 1 was prepared by mixing diisopropylether/acetone/water in 40:15:0.5 volume ratio.

Silica gel (30 Kg, 45 vol) was suspended in the eluent mixture 1 (66.3 Kg, 100 vol), the suspension was stirred for 3 min and loaded in the column.

The crude product was dissolved in the eluent mixture (1 L, 1.5 vol) and charged on the top of the column. The elution was performed and fractions of 15 L were collected and analyzed by TLC. Fractions were combined according to purity and analyzed by HPLC and UPLC.

Selected fractions with desired purity were collected and the solvent was evaporated using a rotary evaporator at temperature of 45° C.±5° C. until dryness. The residue was dissolved in dichloromethane (5 L, 7.5 vol) and the solvent was evaporated again until dryness.

The Compound (I) was stored at 5° C.±3° C.

Silica Gel Filtration Chromatography

Eluent mixture 2 was prepared by mixing distilled dichloromethane and distilled methanol in 30:1 volume ratio.

Silica 75 S (6.6 Kg, 10 vol) was added to eluent mixture 2 (13 Kg, 19.6 vol) and the suspension was stirred and poured to fill the column. Compound (I) was dissolved in dichloromethane (1 L, 1.5 vol) and the solution was loaded on the top of the column.

The elution was performed and fractions were controlled by TLC and the selected fractions with desired purity were collected; the combined fractions were analyzed by HPLC and UPLC.

Fractions were evaporated in a rotary evaporator under vacuum at temperature of 45° C.±5° C. The pure Compound (I) isolated as an oil was stored at 5° C.±3° C.

Treatment with Activated Charcoal (Clarification)

The pure Compound (I) was dissolved in ethanol (6 L, 9 vol) and activated charcoal (60 g, around 9% w/w) was added. The mixture was stirred for 30 min at 20° C.±5° C. and the activated charcoal is removed by filtration. The solvent was evaporated under vacuum at 45° C.±5° C. until constant weight; 649.6 g (1.13 mole) pure Compound (I) was isolated as an oil. The overall yield of the process was 70.8%.

The purity assessment of the isolated Compound (I) was performed by HPLC analysis using the two methods described below, the HPLC assay of Compound (I) was 99.91% (HPLC area %) assessed by HPLC/Method 1.

The Limit of Detection (LoD) and the Limit of Quantification (LoQ) for 15-(6-chlorohexanoyl) ester of bimatoprost of formula (II), 6-{[6-(nitrooxy)hexanoyl]oxy}hexanoic acid bimatoprost ester of formula (III), 5,6-trans-Compound (I) of formula (VII) and 15-epi-Compound (I) of formula (VIII) are reported in Table 1.

The impurities profile of the isolated Compound (I) is reported in Table 2.

Table 3 reports the contents of the impurity 15-(6-chlorohexanoyl) ester of bimatoprost (II) in the Compound (I) prepared according to the processes disclosed in the prior art.

Method 1: the HPLC analysis was performed using the following measurement conditions:

Instrument: Waters HPLC System with PDA detector

Stationary phase: Zorbax RX SIL, 250×4.6 mm, 5 μm

Column temperature: 35° C.

Mobile phase: hexane: Ethanol:acetonitrile:acetic acid=935:60:5:0.5

Run Time: 60 min

Flow rate: 1.5 ml/min

Injected Volume: 20 μl

Detection: UV, 210 nm

Sample solvent: ethanol:hexane 2:8

Method 2: the HPLC analysis was performed to quantify the 15-epi-Compound (I) of formula (VIII) using the following measurement conditions:

Instrument: Waters HPLC System with PDA detector

Stationary phase: Chiralpak AD-H, 250×4.6 mm, 5 μm

Column temperature: 25° C.

Mobile phase: Hexane:Ethanol:TFA—850:150:1

Run Time: 30 min

Flow rate: 1.0 mL/min

Injected Volume: 10 μL

Detection: 210 nm

Sample solvent: Hexane:Ethanol—8:2

TABLE 1

Limit of Detection (LoD) and Limit of Quantification (LoQ) of the impurities

| IMPURITY | LoD % w/w | LoQ % w/w |
|---|---|---|
| 15-(6-chlorohexanoyl) ester of bimatoprost of formula (II) | 0.01 | 0.03 |
| 6-{[6-(nitrooxy)hexanoyl]oxy}hexanoic acid bimatoprost ester of formula (III) | 0.02 | 0.05 |
| (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate (5,6-trans-Compound (I) of formula (VII)) | 0.01 | 0.05 |
| (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate (15-epi-Compound (I) of formula (VIII)) | 0.02 | 0.05 |

TABLE 2

HPLC analysis of the isolated Compound (I) of Example 1 Main and total impurities

| IMPURITY | % (w/w) | Method 1 RT (min) | Method 2 RT (min) |
|---|---|---|---|
| 15-(6-chlorohexanoyl) ester of bimatoprost of formula (II) | <LoD | 15.4 | — |
| 6-{[6-(nitrooxy)hexanoyl]oxy}hexanoic acid bimatoprost ester of formula (III) | <LoD | 22.1 | — |
| (1E,3S)-1-((1R,2R,3S,5R)-2-((2E)-7-(ethylamino)-7-oxohept-2-en-1-yl)-3,5-dihydroxycyclopentyl)-5-phenylpent-1-en-3-yl 6-(nitrooxy) hexanoate (5,6-trans-Compound (I) of formula (VII)) | <LoQ§ | 23.6 | — |
| (1E,3R)-1-((1R,2R,3S,5R)-2-((2Z)-7-(ethylamino)-7-oxohept-2-en-1-yl)-3,5-dihydroxycyclopentyl)-5-phenylpent-1-en-3-yl 6-(nitrooxy) hexanoate (15-epi-Compound (I) of formula (VIII)) | <LoD | — | 13.9 |
| Total impurities | 0.07* | NA | NA |

RT = Retention time

§the measured amount of 5,6-trans-Compound (I) of formula (VII) was 0.04% w/w calculated as medium value of two determinations by HPLC analysis

*HPLC area %

TABLE 3

Summary of the contents of the impurity 15-(6-chlorohexanoyl) ester of bimatoprost (II) in the Compound (I) prepared according to the processes disclosed in the prior art

| | WO 2009/136281 | WO 2019/162149 | WO 2021/023693 |
|---|---|---|---|
| 15-(6-chlorohexanoyl) ester of bimatoprost of formula (II) | 8.34 (HPLC area %) | 0.15-0.24 (% w/w) | 0.11 (HPLC area %) |

The invention claimed is:

1. A process for the preparation of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I)

(I)

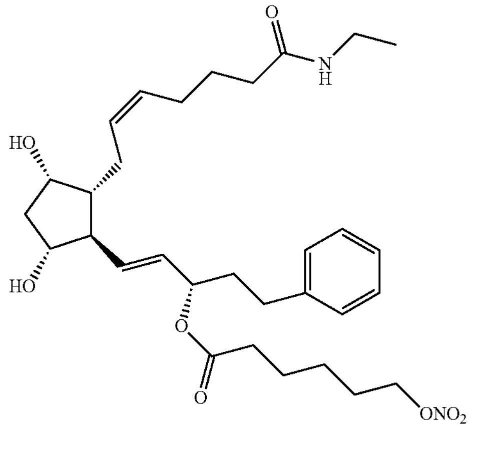

comprising the following steps:

1) reacting bimatoprost with phenylboronic acid in toluene at the refluxing temperature and removing water by azeotropic distillation to obtain bimatoprost phenylboronate of formula (V)

(V)

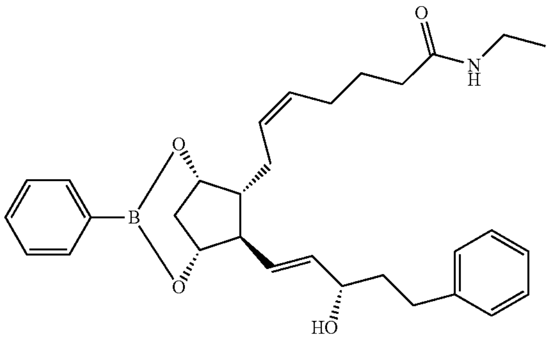

2) cooling down the solution to 25° C. and adding N,N'-diisopropyl carbodiimide, a catalytic amount of dimethylaminopyridine and 6-(nitrooxy)hexanoic acid to obtain (1E,3S)-1-{(1S,5R,6R,7R)-7-[(2Z)-7-(ethylamino)-7-oxohept-2-en-1-yl]-3-phenyl-2,4-dioxa-3-borabicyclo[3.2.1]octan-6-yl}-5-phenylpent-1-en-3-yl 6-(nitrooxy)hexanoate of formula (VI)

(VI)

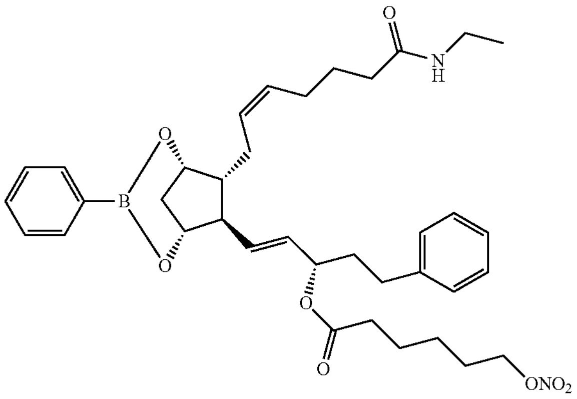

3) removing the phenylboronate protecting group under basic conditions;

4) separating the organic phase and evaporating the solvent;

5) stirring the raw product in dichloromethane, filtering the mixture and evaporating the solvent to obtain the crude compound of formula (I);

6) purifying the crude compound of formula (I) by applying a normal phase gravity silica gel column chromatography using an eluent mixture containing diisopropyl ether, acetone and water in 40:15:0.5 volume ratio;

7) collecting the fractions of appropriate purity and evaporating the solvent to provide pure compound of formula (I);

8) dissolving the pure compound of formula (I) of step 7) in distilled methylene chloride and methanol, purifying the solution by gravity chromatography using an eluent mixture containing distilled methylene chloride and methanol in 30:1 volume ratio and collecting the fractions of appropriate purity and evaporating the solvent to obtain pure compound of formula (I);

9) dissolving the pure compound of formula (I) of step 8) in a ethanol, treating the solution with activated charcoal, thereafter removing the activated charcoal by filtration and removing the solvent by evaporation under vacuum to yield pure hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester;

said process being characterized in that the obtained hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester does not contain the 15-(6-chlorohexanoyl) ester of bimatoprost of formula (II), and contains not more than (≤) 0.20% (HPLC area %) of total impurities.

2. The process according to claim 1 wherein, in the reaction step 1), the bimatoprost:phenyl boronic acid molar ratio is 1:1.1.

3. The process according to claim 1 wherein, in the reaction step 2), N,N'-diisopropyl carbodiimide 2.0 equiv., dimethylaminopyridine 0.2 equiv. and 6-(nitrooxy)hexanoic acid 1.8 to 2.2 equiv. are added.

4. The process according to claim 1, wherein in the reaction step 3) the phenylboronate protecting group is removed using a NaOH solution.

5. The process according to claim 4 wherein the phenylboronate protecting group is removed by quenching the reaction mixture obtained in step 2) with methanol, then adding a mixture of methylene chloride and 6.3 equiv. of NaOH as solution of NaOH 0.5M.

6. The process according to claim 1, wherein, in reaction step 4) the organic phase is washed first with an aqueous solution of sodium hydrogen sulfate and twice with an aqueous solution of NaCl 15% w/w.

* * * * *